United States Patent [19]
Mordechai et al.

[11] Patent Number: 5,853,996
[45] Date of Patent: Dec. 29, 1998

[54] DETECTION OF CHRONIC FATIGUE SYNDROME BY INCREASED APOPTOSIS AND CELL CYCLE ARREST OF PERIPHERAL BLOOD MONONUCLEAR CELLS

[75] Inventors: Eli Mordechai; Aristo Vojdani, both of Los Angeles, Calif.

[73] Assignee: Immunosciences Lab, Inc., Beverly Hills, Calif.

[21] Appl. No.: 843,951

[22] Filed: Apr. 17, 1997

Related U.S. Application Data

[62] Division of Ser. No. 766,677, Dec. 13, 1996.

[51] Int. Cl.$^6$ .............................. C12N 1/68; G01N 33/53
[52] U.S. Cl. .............................. 435/6; 435/7.24; 435/372
[58] Field of Search .............................. 435/6, 7.24, 372

[56] References Cited

PUBLICATIONS

Swanink et al., J. of Infectious Diseases, vol. 173, 1996, pp. 460–463, Mar. 96.
E. Barker, et al., "Immunologic Abnormalities Associated with Chronic Fatigue Syndrome", *Clin. Infec. Diseases* 18(Suppl. 1):S136–S141 (1994).
M. Becker–Andre, et al., "Absolute mRNA quantification using the polymerase chain reaction (PCR). A novel approach by a PCR aided transcript titration assay (PATTY)", *Nucleic Acids Research* 17(22):9437–9446 (1989).
C. Bisbal, et al., "Cloning and Characterization of a RNase L Inhibitor", *The Jour. of Biol. Chem.* 270(22):13308–13317 (1995).
A. Boyum, "Isolation of Mononuclear Cells and Granulocytes from Human Blood", *Norwegian Defence Research Establishment,* Division for Toxicology, Kjeller, Norway, Paper IV, 77–89, 1968.
C. Buffet–Janvresse, et al., "Enhanced Level of Double–Stranded RNA–Dependent Protein Kinase in Peripheral Blood Mononuclear Cells of Patients with Viral Infections", *Jour. Of Interferon Research* 6:85–96 (1986).
G.B. Corcoran, et al., "Contemporary Issues In Toxicology Apoptosis: Molecular Control Point in Toxicity", *Toxicology and Applied Pharmacology* 128:169–181 (1994).
D. Ferbus, et al., "The 2'5' Oligoadenylate Synthetase Has A Multifunctional 2'5' Nucleotidyl–Transferase Activity", *Biochem. and Biophys. Res. Communications* 100(2):847–856 (1981).
T.A. Fleisher, et al., "Flow Cytometry", *Clinical Immunology Principles and Practice* Chapter 141:2110–2123 (1996).
G. Floyd–Smith, et al., "Interferon Action: RNA Cleavage Pattern of a (2'–5')Oligoadenylate–Dependent Endonuclease", *Science* 212:1030–1032 (1981).
A. Fraser, et al., "Biochemistry of cell death", *Current Opinion in Neurobiology* 6:71–80 (1996).
K. Fukuda, M.D., et al., "The Chronic Fatigue Syndrome: A Comprehensive Approach to Its Definition and Study", *Annals of Internal Medicine* 121(12):953–959 (1994).

G. Gilliland, et al., "Analysis of cytokine mRNA and DNA: Detection and quantitation by competitive polymerase chain reaction", *Proc. Natl. Acad. Sci. USA* 87:2725–2729 (1990).
A.G. Hovanessian, "Interferon–Induced and Double–Stranded RNA–Activated Enzymes: A Specific Protein Kinase and 2',5'–Oligoadenylate Synthetases", *Journal of Interferon Research* 11:199–205 (1991).
N.G. Klimas, et al., "Immunologic Abnormalities in Chronic Fatigue Syndrome", *Jour. of Clinical Microbiology* 28(6):1403–1410 (1990).
A.E. Koromilas, et al., "Malignant Transformation by a Mutant of the IFN–Inducible dsRNA–Dependent Protein Kinase", *Science* 257:1685–1689 (1992).
S.B. Lee, et al., "The Interferon–Induced Double–Stranded RNA–Activated Protein Kinase Induces Apoptosis", *Virology* 199:491–496 (1994).
P. Lengyel, "Tumor–suppressor genes: News about the interferon connection", *Proc. Natl. Acad. Sci. USA* 90:5893–5895 (1993).
T. Lion, "Clinical implications of qualitative and quantitative polymerase chain reaction analysis in the monitoring of patients with chronic myelogenous leukemia", *Bone Marrow Transplantation* 14:505–509 (1994).
E.F. Meurs, et al., "Molecular Cloning and Characterization of the Human Double–Stranded RNA–Activated Protein Kinase Induced by Interferon", *Cell* 62:379–390 (1990).
E.F. Meurs, et al., "Tumor suppressor function of the interferon–induced double–stranded RNA–activated protein kinase", *Proc. Natl. Acad. Sci. USA* 90:232–236 (1993).
E. Mordechai, et al., "Activation of the Interferon–Inducible Enzymes, 2',5'–Oligoadenylate Synthetase and PKR by Human T–Cell Leukemia Virus Type I Rex–Response Element", *Virology* 206:913–922 (1995).
L.J.A. Morrison, et al., "Changes in natural killer cell phenotype in patients with post–viral fatigue syndrome", *Clin. exp. Immunol.* 83:441–446 (1991).
A. Pena, et al., "Regulation of Human Ornithine Decarboxylase Expression by the c–MycMax Protein Complex", *The Jour. of Biological Chemistry* 268(36):27277–27285 (1993).
S. Pestka, et al., "Interferons and Their Actions", *Ann. Rev. Biochem.* 56:727–777 (1987).
T. Salehzada, et al., "2',5'–Oligoadenylate–dependent RNase L Is a Dimer of Regulatory and Catalytic Subunits" *The Jour. of Biological Chemistry* 268(11):7733–7740 (1993).
P.D. Siebert, et al., "PCR Mimics: Competitive DNA Fragments for Use as Internal Standards in Quantitative PCR", *BioTechniques* 14(2):244–249 (1993).

(List continued on next page.)

*Primary Examiner*—Frank C. Eisenschenk
*Assistant Examiner*—Patrick Nolan
*Attorney, Agent, or Firm*—Knobbe, Martens, Olson & Bear, LLP

[57] ABSTRACT

A method for diagnosing chronic fatigue syndrome in an individual. Peripheral blood monocytes are isolated and p68 kinase activity, mRNA levels, protein levels, apoptosis and cell cycle analysis are measured. Significantly increased levels of any of these compared to healthy control individuals indicates the presence of chronic fatigue syndrome.

3 Claims, 7 Drawing Sheets

OTHER PUBLICATIONS

R.H. Silverman, et al., "Control of the ppp(A2'p)$_n$A System in HeLa Cells", *Eur. J. Biochem.* 124:131–138 (1982).

R.J. Suhadolnik, et al., "Upregulation of the 2–5A Synthetase/RNase L Antiviral Pathway Associated with Chronic Fatigue Syndrome", *Clinical Infectious Diseases* 18(Suppl. 1):S96–S104 (1994).

D.H. Wreschner, et al., "Interferon action—sequence specificity of the ppp(A2'p)$_n$A–dependent ribonuclease", *Nature* 289:414–417 (1981).

A.H. Wyllie, et al., "Cell Death: The Significance of Apoptosis", *International Review of Cytology* 68:251–306 (1980).

A. Zhou, et al., "Expression Cloning of 2–5A–Dependent RNAase: A Uniquely Regulated Mediator of Interferon Action", *Cell* 72:753–765 (1993).

*Immunosciences Lab. Inc.,* new product announcement, (Jan. 1996).

DETECTION OF CHRONIC FATIGUE SYNDROME BY INCREASED APOPTOSIS AND CELL CYCLE ARREST OF PERIPHERAL BLOOD MONONUCLEAR CELLS

This application is a divisional of U.S. patent application Ser. No. 08/766,677, filed Dec. 13, 1996, pending.

FIELD OF THE INVENTION

The present invention relates to the diagnosis of chronic fatigue syndrome (CFS) by detecting elevated levels of double stranded RNA-activated protein kinase (p68 kinase or PKR) which leads to increased apoptotic cell populations and cell arrest in the late S and $G_2$/M boundaries of the cell cycle. The PKR gene product is involved in the interferon-mediated antiviral, antiproliferative pathway.

BACKGROUND OF THE INVENTION

Chronic Fatigue Syndrome (CFS) is a systemic disorder defined by the Centers for Disease Control (CDC) as self-reported persistent or relapsing fatigue lasting six or more months (Fukuda et al., Ann. Intern. Med., 121: 953–959, 1994). Patients with CFS tend to have individualistic symptoms triggered by stress or unknown factors including low grade fever, sore throat, headache, painful lymph nodes, muscle weakness, irritability, inability to concentrate; depression, irregular heartbeat and neuropsychological problems. Although the precise nature and cause of CFS is unknown, there is some clinical and serological association with all of the human herpes viruses, particularly Epstein-Barr virus (EBV) and Human B-lymphotropic virus (HBLV). CFS may involve physiological manifestations of neurological influences on immune function by neurohormones or other immunomodulators of T-lymphocyte function. Upon binding to various lymphocyte surface antigens, viruses induce secretion of lymphokines which may interfere with immune response regulation including mucosal, humoral and cellular immunity.

Many reports have described a decrease in natural killer (NK) cell-mediated cytotoxic activity and abnormal production of tumor necrosis factor α (TNF-α), interleukin-1α and interferon (IFN) (Klimas et al., J. Clin. Microbiol., 28: 1403–1410, 1990; Morrison et al., Clin. Exp. Immunol. 83: 441–446, 1991; Barker et al., Clin Infect. Dis., 18: S136–S141, 1994). The interferons are a family of antiviral and antiproliferative cytokines which exert their pleiotropic effects through the induction of several antiviral genes (Lengyel, Proc. Natl. Acad. Sci. U.S.A., 90: 5893–5895, 1993; Pestka et al., Annu. Rev. Biochem., 56: 727–777, 1987).

The IFN-induced antiviral and antiproliferative pathways include two gene products; 2',5'-oligoadenylate synthetase (2-5OAS) and a double-stranded, RNA-activated protein kinase also called p68 kinase, P1 kinase and protein kinase RNA (PKR). This protein is referred to as PKR throughout the present application. 2-5OAS, a double stranded RNA (dsRNA) dependent enzyme converts ATP to 2',5'-oligoadenylates (2-5A) via a 2',5'-phosphodiester bond (Ferbus et al., Biochem. Biophys. Res. Commun., 100: 847–856, 1981; Mordechai et al., Virology, 206: 913–922, 1995). Subnanomolar concentrations of 2-5A activate a latent endonuclease, RNase L, which is the terminal enzyme in the 2-5A system (Zhou et al., Cell, 72: 753–765, 1993). Activated RNase L degrades mRNA and rRNA on the 3' side of a UpNp sequence, resulting in inhibition of viral and cellular protein synthesis (Floyd-Smith et al., Science, 212: 1029–1032, 1981; Wreschner et al., Nature, 289: 414–417, 1981).

RNase L is also regulated by a 68 kDa RNase L inhibitor (RLI) which binds to RNase L and inhibits the binding of 2-5A (Bisbal et al., J. Biol. Chem., 270: 13308–13317, 1995). RLI levels are not regulated by IFN, although IFN treatment of cells resulted in a three fold increase in RNase L and 2-5OAS mRNA levels. Copending U.S. patent Ser. No. 08/727,708, the entire contents of which are hereby incorporated by reference, discloses the down regulation of RLI in CFS patients compared to healthy controls. Down-regulation of RLI results in uncontrolled activation of RNase L, followed by enhanced cellular RNA turnover.

Another IFN-mediated pathway involves PKR. Upon activation by double stranded viral RNA, PKR is autophosphorylated and phosphorylates the α subunit of eukaryotic initiation factor 2 (eIF-2α), an enzyme involved in protein synthesis, resulting in inhibition of the translation initiation process (Pestka et al., ibid.; Hovanessian, J. Interferon Res., 11: 199–205, 1991). PKR expression has also been implicated in neoplastic cell growth. The introduction of catalytically inactive PKR into NIH 3T3 cells resulted in the formation of a transformed cell line capable of inducing tumor formation in nude mice. The catalytically inactive PKR acted as a transdominant negative counterpart to the resident wild type PKR, indicating that PKR is a tumor suppressor (Koromilas et al., Science, 257: 1685–1689, 1992; Lengyel, ibid 1993; Meurs et al. Proc. Natl. Acad. Sci. U.S.A., 90: 232–236, 1993). PKR autophosphorylation and the phosphorylation of eIF-2α are inhibited by a 58 kDa PKR inhibitor. During viral infections and cancer, PKR protein levels increased up to about five fold over basal levels (Buffet-Janvresse, J. Interferon Res., 6: 85–96, 1996; Mordechai et al., Virology, 206: 913–922, 1995). Expression and activation of PKR in HeLa cells induced programmed cell death (apoptosis) (Lee et al., Virology, 199: 491–496, 1994).

Apoptosis is a physiological mode of programmed cell death in which the cell actively participates in the process. Morphologic features of apoptosis include cell shrinkage, cytoplasmic condensation and the induction of double strand DNA fragmentation at linker regions between nucleosomes (for review see Fraser et al., Curr. Opin. Neurobiol., 6: 71–80, 1996). Apoptosis was stimulated in human leukemic cell lines by apogens including regulatory proteins (i.e. tumor suppressors), hormones and chemicals (Corcoran et al., Toxicol. Applied Pharmacol., 128: 169–181, 1994). Induction of apoptosis through immune defense mechanisms plays an important role in the destruction of cancer cells and virus infected cells. Inhibition of apoptosis may comprise one mechanism of tumor promotion; however, uncontrolled apoptosis can be detrimental to developing tissues.

The present invention relates PKR and apoptosis to the detection of individuals with CFS.

SUMMARY OF THE INVENTION

One embodiment of the present invention is a method of diagnosing chronic fatigue syndrome (CFS) in an individual, comprising the steps of:
  isolating peripheral blood mononuclear cells (PBMCs) from the individual;
  determining the amount of protein kinase RNA (PKR) mRNA or protein present in the PBMCs from the individual; and comparing the amount of PKR mRNA or protein from the individual to an expected amount of PBMCs from a control individual known not to have CFS, wherein an increase in the amount in the individual compared to the control individual indicates the presence of CFS.

Preferably, the determining step comprises quantitative competitive polymerase chain reaction (Q/C PCR). Alternatively, the mRNA determining step comprises Northern blotting or RNase protection assay. Advantageously, the PKR protein determining step comprises an immunoassay. Preferably, the immunoassay comprises Western blotting or enzyme linked immunosorbent assay. The method may further comprise determining the expected amount of PKR mRNA or protein from the control individual by measuring the amount of PKR mRNA or protein in PBMCs isolated from the control individual.

According to one aspect of this preferred embodiment, the expected amount of PKR mRNA is about 500 copies/$\mu$g RNA in normal individuals and about 3,500 copies/$\mu$g RNA in CFS individuals.

The present invention also provides a method of diagnosing chronic fatigue syndrome (CFS) in an individual, comprising the steps of:
 isolating peripheral blood mononuclear cells (PBMCs) from the individual;
 determining the activity of PKR present in the PBMCs from the individual; and
 comparing the activity from the individual to an expected amount of PBMCs from a control individual known not to have CFS, wherein an increase in the activity in the individual compared to the control individual indicates the presence of CFS.

Preferably, the determining step comprises an autophosphorylation assay or exogenous substrate phosphorylation assay. The method may further comprise determining the expected amount of PKR mRNA or protein from the control individual by measuring the activity of PKR in PBMCs isolated from the control individual.

Another embodiment of the invention is a method of diagnosing chronic fatigue syndrome (CFS) in an individual, comprising the steps of:
 isolating peripheral blood mononuclear cells (PBMCs) from the individual;
 determining the number of apoptotic PBMCs present in the PBMCs from the individual; and
 comparing the number of apoptotic PBMCs present in PBMCs from the individual to an expected amount of apoptotic PBMCs from a control individual known not to have CFS, wherein an increase in the number of apoptotic PBMCs in the individual compared to the control individual indicates the presence of CFS.

Preferably, the determining step comprises fluorescently or radioactively labeling DNA strand breaks in said PBMCs and detecting said labeled strand breaks. Alternatively, the determining step comprises isolation and analysis of low molecular weight DNA from the PBMCs. This preferred embodiment may further comprising determining the expected PKR activity from the control individual by measuring the amount of PKR mRNA or protein in PBMCs isolated from the control individual.

Still another embodiment of the invention is a method of diagnosing chronic fatigue syndrome (CFS) in an individual, comprising the steps of:
 isolating peripheral blood mononuclear cells (PBMCs) from the individual;
 determining the number of PBMCs from the individual arrested in the late S and $G_2$/M stages of the cell cycle; and
 comparing the number of arrested PBMCs from the individual to an expected amount of arrested PBMCs from a control individual known not to have CFS, wherein an increase in the number of arrested PBMCs in the individual compared to the control individual indicates the presence of CFS.

Preferably, the determining step comprises fluorescent labeling of said PBMCs and detection of the labeled PBMCs by flow cytometry. The method may further comprise determining the expected number of arrested PBMCs in the control individual by measuring the amount of arrested PBMCs isolated from the control individual.

DETAILED DESCRIPTION OF THE PREFERRED EMBODIMENTS

The present invention includes the discovery that PKR mRNA and protein levels are significantly increased in lymphocytes of CFS patients compared to unaffected individuals. In addition, greatly increased apoptosis was observed in lymphocytes of CFS patients. In the examples described below, PKR mRNA levels were determined by performing quantitative competitive polymerase chain reaction (Q/C PCR) on PCR-synthesized cDNA using mRNA isolated from CFS or normal human lymphocytes. The Q/C PCR analysis we conducted indicates a statistically significant increase in PKR mRNA present in the peripheral blood mononuclear cells (PBMC) of patients with CFS compared to PKR mRNA levels present in PBMC of healthy individuals.

Although the specific examples for the detection of PKR mRNA levels were performed using Q/C PCR, one of ordinary skill in the art will appreciate that any other method capable of detecting PKR mRNA levels is also within the scope of the present invention. One such method is conventional Northern blotting, in which either total RNA or mRNA is isolated from PBMCs of an individual suspected of having CFS. The RNA is analyzed by agarose gel electrophoresis, transferred to a nitrocellulose, nylon or other suitable membrane, and incubated with a labeled oligonucleotide probe complementary to a region of the PKR mRNA sequence. Because the PKR cDNA sequence is known (Meurs et al., *Cell*, 62: 370–390, 1990), such probes can easily be determined and synthesized according to well known methods. Another well known contemplated method for detecting increased PKR mRNA levels is the RNase protection assay. This method is based on the resistance of RNA—pe RNA hybrids to RNase T1 digestion. Total mRNA isolated from PBMCs is incubated with labeled PKR probe to allow hybrid formation followed by addition of RNase. All mRNA with the exception of PKR mRNA will be degraded. RNase is then inactivated, followed by quantitation of PKR mRNA by gel electrophoresis (Pena et al., *J. Biol. Chem.*, 268: 27277–27285, 1993).

Polyclonal antibodies to PKR were generated by conjugating each of two peptides contained within the PKR amino acid sequence to an immunogenic carrier protein and injecting the conjugate into rabbits. The resulting antisera recognized PKR in cytoplasmic extracts of PBMCs. A significant increase in PKR protein levels was observed in CFS individuals compared to healthy controls as determined by Western blotting of PBMC cytoplasmic extracts. Monoclonal antibodies to PKR can be generated using conventional hybridoma technology and are also contemplated for determining PKR protein levels. In addition, the detection of PKR protein levels by conventional immunoassays (i.e. enzyme-linked immunosorbent assay) is also within the scope of the invention.

In addition to detecting increased PKR mRNA and protein levels in CFS patients, PKR activity can also be determined. An increase in PKR activity is also a positive indicator of CFS. PKR activity was assayed by an autophosphorylation assay (Mordechai et al., *Virology*, 206: 913–922, 1995, hereby incorporated by reference). Briefly, cytoplasmic PBMC extracts from both CFS patients and control individuals were incubated in the presence of poly(rI)-poly(rC), magnesium ion and [$\gamma$-$^{32}$P]dATP. Quantitation of autophosphorylation was performed by scanning autoradiograms of 10% SDS gels. In CFS individuals, PKR autophosphorylation paralleled the induction of PKR mRNA and protein levels. The activity of PKR can also be measured by phosphorylation of exogenous substrates (i.e. histones), a widely used assay for protein kinase activity. In this assay, extracts prepared from PBMCs of CFS individuals and healthy controls were incubated with poly(rI)-poly(rC) Sepharose (Pharmacia). Rhw PKR-bound poly(rI)-poly(rC) was washed with PBS and further incubated with calf thymus histone (H II A, Sigma) in the presence of [$\gamma$-$^{32}$P] ATP (Buffet-Janvresse et al., *J. Interferon Res.*, 6: 85–96, 1986).

PBMCs isolated from CFS individuals contained significantly greater numbers of apoptotic cells compared to healthy control individuals as determined by flow cytometry of fluorescent dUTP-labeled and stained hypodiploid apoptotic cells. For a discussion of flow cytometry, see Fleisher et al. (*Clinical Immunology Principles and Practice*, Rich, R. et al. eds., Mosby Press, Carlsbad, Calif., pp. 2110–2123, 1996). DNA fragmentation of apoptotic cells was evaluated by assessing the proportion of hypochromic stained cells in the flow cytometer as described in Example 7. The determination of apoptosis by other methods is also contemplated, including labeling of DNA breaks with radiolabeled nucleosides and DNA ladder analysis. In the DNA ladder method, low molecular weight DNA is isolated and analyzed by agarose gel electrophoresis. A DNA ladder corresponding to cleavage of DNA into 180 bp multimers is observed only if apoptosis occurs (Wyllie et al., *Int. Rev. Cytol.*, 68: 251–306, 1980, incorporated by reference). The PKR inhibitor 2-aminopurine (2-AP), a competitive inhibitor of ATP binding to PKR, significantly decreased the apoptotic cell population in CFS individuals. The decreased apoptotic cell population in the presence of 2-AP indicates that the induction of apoptosis in CFS individuals is caused by elevated PKR levels.

To determine whether the induction of apoptosis in PBMC isolated from CFS individuals represented a discrete block in cell cycle progression, PBMC isolated from CFS and control individuals were analyzed by flow cytometry. The non-apoptotic cell population in PBMCs isolated from CFS individuals consisted of cells arrested in the late S and G2/M boundaries compared to healthy controls. The arrest was characterized by increased S and G2/M phases of the cell cycle. Such an abnormality in cell cycle progression indicates abnormal mitotic cell division.

The following examples provide illustrative methods for carrying out the preferred steps in conjunction with the practice of the present invention. As such, these examples are provided for illustration purposes only and are not intended to limit the invention.

PBMCs were isolated from both CFS and healthy individuals as described in the following example.

EXAMPLE 1

Isolation of PBMCs

Thirty patients with CFS (13 males, 17 females) and 15 healthy control individuals (8 males, 7 females) were used as sources of PBMCs. All subjects met the epidemiological case definition of CFS established by the CDC. Controls were randomly selected volunteers employed by Immunosciences Lab, Inc., Beverly Hills, Calif., or had been seen by physicians for routine physical examinations unrelated to the existence of CFS or any other disorder. Venous blood (10 ml) was obtained by venipuncture. PBMCs were isolated by Ficoll-Hypaque (Sigma, St. Louis, Mo.) gradient centrifugation of heparinized blood at 1,600 rpm for 30 min. as described (Boyum et al., *Scand. J. Clin. Lab. Invest.*, 21: 77–89, 1968). The lymphocyte ring was isolated, rinsed twice with phosphate-buffered saline (PBS) and stained with Trypan Blue to determine cellular viability.

RNA was isolated from PBMCs as described in the following example.

EXAMPLE 2

Isolation of RNA and Production of cDNA

RNA was extracted from PBMCs with TRIZOL™ reagent (GIBCO BRL, Gaithersburg, Md.) as described by the manufacturer. Briefly, PBMCs were suspended in 1 ml TRIZOL™ reagent followed by addition of 200 $\mu$l chloroform. The cell suspension was shaken in an orbital shaker, then incubated for 10 min at room temperature to allow phase separation. Samples were centrifuged (12,000 rpm, 10 min, 4° C.) and the aqueous phase was transferred to a fresh tube. Isopropanol (500 $\mu$l) was added to each tube followed by incubation at -70° C. for 1 hour to precipitate RNA. Samples were centrifuged (12,000 rpm, 20 min, 4° C.) and the resulting RNA pellet was washed with 70% ethanol and dissolved in 10 $\mu$l diethyl pyrocarbonate (DEPC)-treated water. One $\mu$l was used for spectrophotometric quantitation. To eliminate DNA contamination, the extracted RNA was treated with DNase I (amplification grade, GIBCO BRL) as described by the manufacturer.

Total RNA was converted to cDNA using the GENE AMP™ RNA PCR kit (Perkin-Elmer, Norwalk, Conn.). Each reaction mixture (20 $\mu$l total volume) contained 10 $\mu$l RNA (approx. 2 $\mu$g), 2.5 $\mu$M oligo d(T)$_{16}$, 1 mM dNTPs, 5 mM MgCl$_2$, 2 µl 10× PCR buffer II, 1 µl MULV RNase inhibitor (10 U/µl) and 2.5 µl MMLV reverse transcriptase (50 U/µl). Reaction mixtures were incubated at 42° C. for 20 min, then at 85° C. for 5 min.

Internal control DNA fragments were synthesized for use in Q/C PCR as described in the following example. Q/C PCR is an amplification technique based on a competitive approach using non-homologous internal DNA standards. The internal controls are DNA fragments constructed for use in competitive PCR amplification for quantitation of target mRNA levels (Gilliland et al., *Proc. Natl. Acad Sci. USA.,* 87: 2725, 1990; Becker-Andre, *Nucl. Acids Res.,* 17: 9437, 1989; Siebert et al., *BioTechniques,* 11: 244–249, 1993, the entire contents of which are hereby incorporated by reference). Each internal standard consists of a heterologous DNA fragment with primer templates that are recognized by a pair of gene-specific (composite) primers. These templates "mimic" the target and are amplified during PCR. This mimic competes with the target DNA for the same primers and thus acts as an internal standard.

To construct the internal standard, two rounds of PCR amplification are performed. In the first PCR reaction, two composite primers are used, each of which contains the target gene primer sequence attached to a short stretch of sequence designed to hybridize to opposite strands of a "mimic" DNA fragment. The desired primer sequences are thus incorporated during the PCR amplification. A dilution of the first PCR reaction is then amplified again using only the gene-specific primers which ensures that all PCR mimic molecules have the complete gene-specific primer sequences. Following the second PCR amplification, the PCR mimic is purified by passage through a column.

Serial dilutions of PCR mimics are added to PCR amplification reactions containing constant amounts of the target cDNA sequence. The PCR mimic and target template thus compete for the same primers in the same reaction. By knowing the amount of PCR mimic added to the reactions, the amount of target template and initial mRNA levels can be determined.

EXAMPLE 3

Synthesis of Internal PKR Control DNA Fragments

An internal control (mimic) DNA fragment was synthesized using the PCR MIMIC™ construction kit (Clontech, Palo Alto, Calif.) according to the manufacturer's instructions. Briefly, 4 ng of a 576 bp neutral fragment (BamHI/EcoRI fragment of the v-erbB gene) (SEQ ID NO: 1) was used as a template with composite PKR primers. The primers were:

| | |
|---|---|
| 5'-GGTCAAAGACTAAGTGCCCGCAAGT-GAAATCCTCCTCCG-3' | (SEQ ID NO: 2) |
| 3'-CCTTTCTGTTTCTGCAGCTGGTATCTT GAGTCCATGGG-5' | (SEQ ID NO: 3) |

PCR reaction mixtures (50 µl) were subjected to 20 cycles of PCR (94° C. for 45 sec, 60° C. for 45 sec, 72° C. for 90 sec) in a DNA thermal cycler. The amplified PCR product was diluted 1:100 and an aliquot (2 µl) was subjected to a second round of PCR amplification under the same conditions using the PKR target primers in a final reaction volume of 100 µl. The PCR product was purified using a pre-spun Chroma column (Clontech) as described by the manufacturer. The mimic DNA fragment was quantitated by electrophoresis and serial dilutions were prepared for Q/C PCR.

EXAMPLE 4

Quantitative Competitive PCR

Q/C PCR was performed essentially as described (Lion, *Bone marrow Transplantation,* 14: 505–509, 1994). Aliquots of cDNA (0.2 µg) prepared as described in Example 2 were added to serially diluted mimic DNA. The Q/C PCR reaction mixture (50 µl) contained the 761 bp mimic DNA, 7 pmol (1 µl) of each PKR gene-specific target primer (5'-GGTCAAAGACTAAGTGCC-3'; SEQ ID NO: 4 and 3'-CCTTTCTGTTTCTGCAG-5'; SEQ ID NO: 5), 2.5 mM MgCl$_2$, 0.25 mM dNTPs, 5 µl 10× PCR buffer (final conc. 10 mM Tris-HCl, pH 8.3, 50 mM KCl, 20 mM MgCl$_2$), and 2.5 units Taq DNA polymerase. Reaction mixtures were heated to 94° C. for 3 min, then subjected to 30 cycles of PCR (94° C. for 35 sec, 54° C. for 1 min, 72° C. for 1 min). Following the final PCR cycle, a 10 min. elongation step at 72° C. was performed. Aliquots (25 µl) of the PCR reaction were analyzed by electrophoresis on 3% Nusieve/agarose (3:1) (FMC) gels in the presence of 0.5 µg/ml ethidium bromide. The concentration of the internal standards and PKR were measured by scanning the ethidium bromide stained gel using a digital imaging densitometer (Alpha Inotech Corp.). Because the PCR-amplified PKR fragment (761 bp) is larger than its internal standard counterpart (576 bp), it exhibits slower migration on an agarose gel. The concentration ratio of the internal controls divided by the concentration of PKR was plotted against the input concentration of the internal standards per tube. The amount of PKR cDNA present in the reaction mixture was defined as the amount of internal control present where the concentration ratio was equal to the PCR product.

Figure 1:
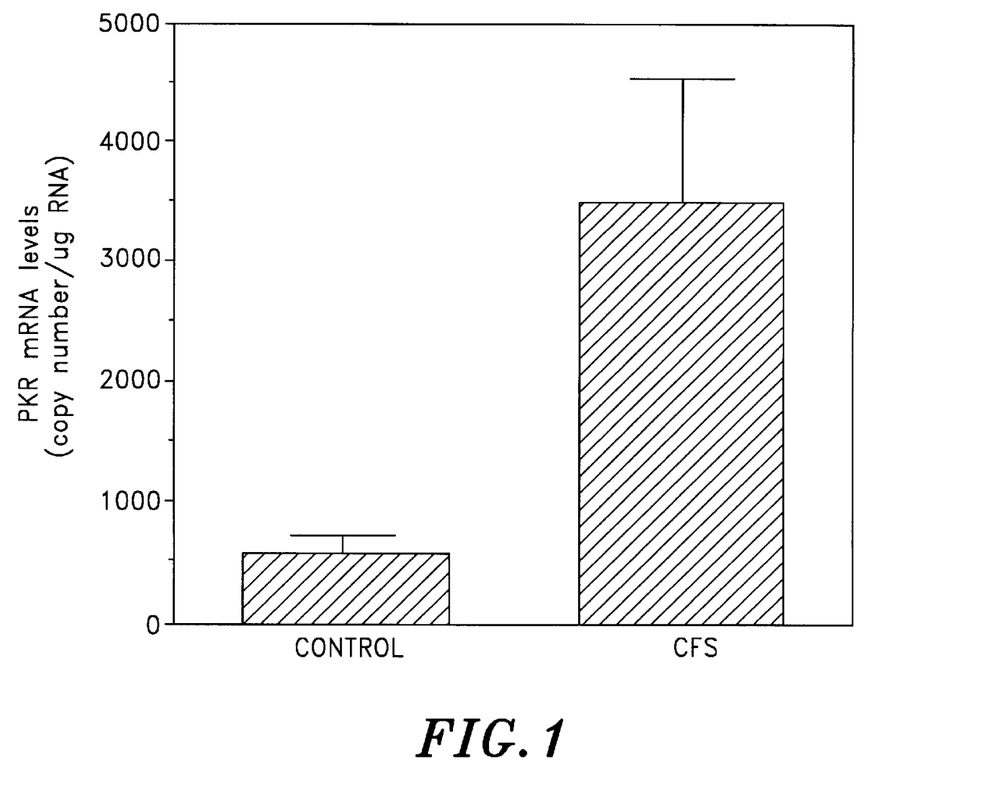
FIG. 1 shows the average PKR mRNA levels in CFS individuals and healthy control individuals.

PKR mRNA levels in PBMC from 15 healthy controls ranged from 200–1,000 PKR mRNA molecules per µg RNA (mean basal level=562, standard error=162). The mean value for the PKR mRNA present in PBMC of CFS patients (n=30) was significantly higher compared to healthy control individuals (CFS mean basal level=3538, standard error=1050) (P<0.0094, Mann-Whitney U-test) (FIG. 1). CFS individuals A1–A3 exhibited increased PKR expression (1300, 5300, 5300 copy number/µg RNA, respectively) as compared to healthy controls (200 PKR mRNA molecules/µg RNA).

EXAMPLE 5

Generation of Antibodies to PKR

Two peptides contained within the PKR protein sequence were synthesized by CHIRON® using Multipin™ technology. The peptides were as follows:

| | |
|---|---|
| HVKALAKLDHVNIVGC | (SEQ ID NO: 6) |
| CYIGLINRIAQKKRLTVNY | (SEQ ID NO: 7) |

The synthesized peptides were analyzed for purity by mass spectrometry (71% and 76%, respectively) and coupled to keyhole limpet hemocyanin (KLH) using standard methods. Rabbits were injected subcutaneously with 1 mg of conjugate in Freund's complete adjuvant and boosted twice at two week intervals with 0.5 mg conjugate in Freund's incomplete adjuvant. Antibody titers in rabbit sera were measured by ELISA using the carrier free peptides.

EXAMPLE 6

Determination of PKR Protein Levels

PBMCs were harvested from blood of both CFS and normal individuals by centrifugation (1,000× g, 10 min, 25° C.). PBMC were lysed in 20 mM HEPES, pH 7.5, 120 mM KCl, 5 mM MgCl$_2$, 1 mM dithiothreitol (DTT), 10% glycerol, 0.5% Nonidet™-P40), vortexed for 2 min and incubated at room temperature for 5 min. Cytoplasmic extracts were isolated by centrifugation (10,000× g, 5 min, 25° C.) and stored at −80° C. Western blot analysis was performed on these cytoplasmic extracts to determine whether the observed increase in PKR mRNA in CFS individuals was accompanied by an increase in PKR protein levels.

Cytoplasmic extracts were subjected to SDS-PAGE on 10% acrylamide gels. Proteins were electrophoretically transferred to nitrocellulose (Whatman) in 25 mM Tris-HCl, pH 8.6, 120 mM glycine, 20% methanol) at 4° C. overnight (50 mA). The filter was blocked by incubation for 2 hours at 25° C. in 10 mM Tris-HCl, pH 8.0, 150 mM NaCl, 0.1% Tween-20 (Sigma) (TBST) containing 5% nonfat dry milk. TBST-milk was removed and the filter was washed 5×5 min in TBST. The filter was then incubated in TBST containing PKR antibody (1:1000 dilution) for 1 hour at 25° C. The primary antibody solution was removed and the blot washed 5×5 min with TBST at room temperature. The filter was then incubated with rabbit anti-IgG conjugated horseradish peroxidase (HRP) (Amersham) diluted 1:2,500 in TBST for 1 hour at room temperature, followed by washing 5×5 min with TBST. Bound secondary antibody HRP conjugate was detected using chemiluminescence reagents (Amersham).

Figure 2A:
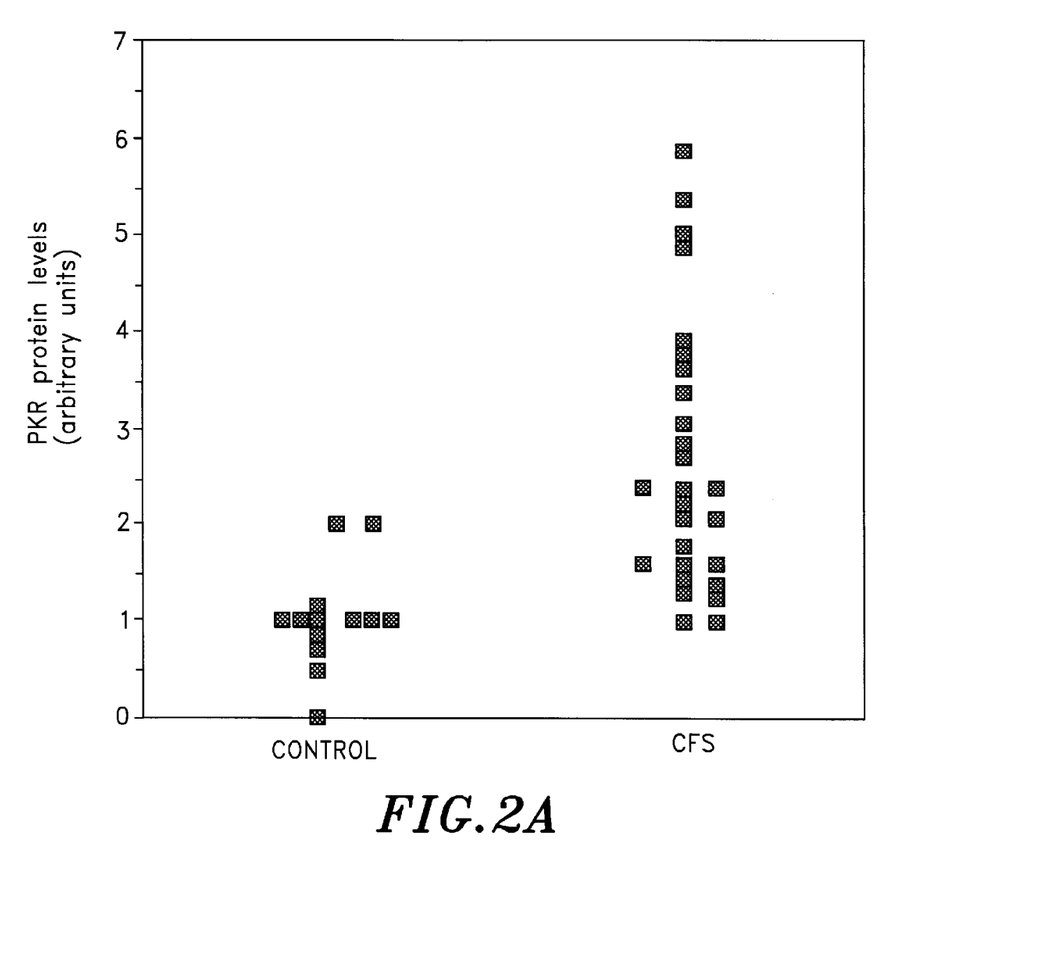
FIG. 2 shows PKR protein levels and statistical analysis of 30 CFS patients compared to 15 healthy control individuals.
Figure 2B:
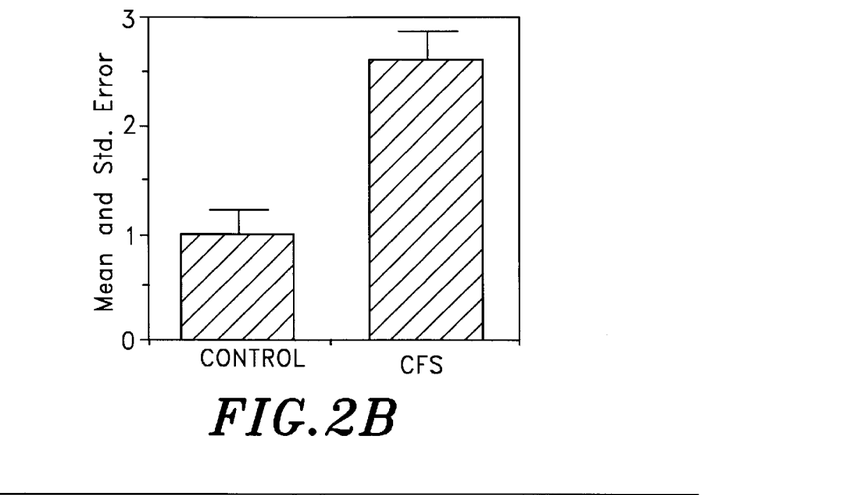
Figure 3A:
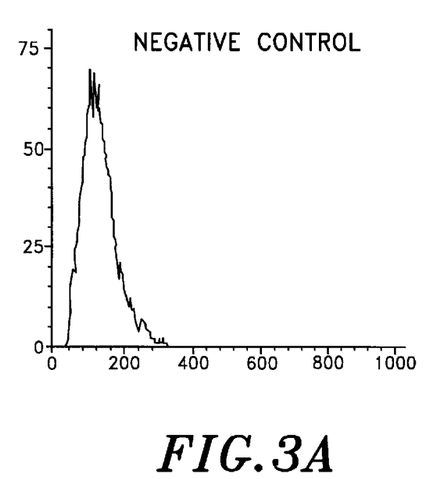
FIG. 3 shows the increased apoptosis observed in CFS individuals. The negative control is the human lymphocytic cell line HL-60 (ATCC CCL240). The positive control is HL-60 cells treated with camptotecin, a known inducer of apoptosis.
Figure 3B:
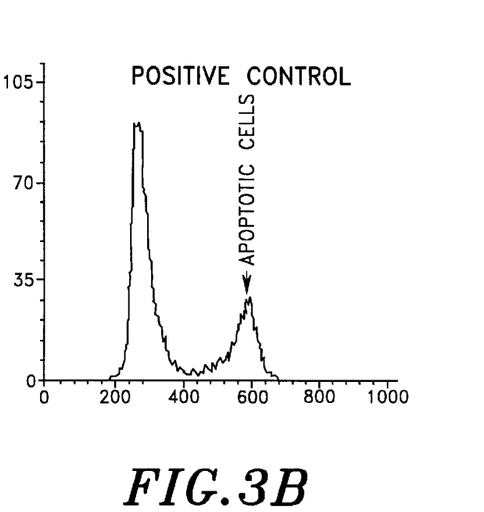
Figure 3C:
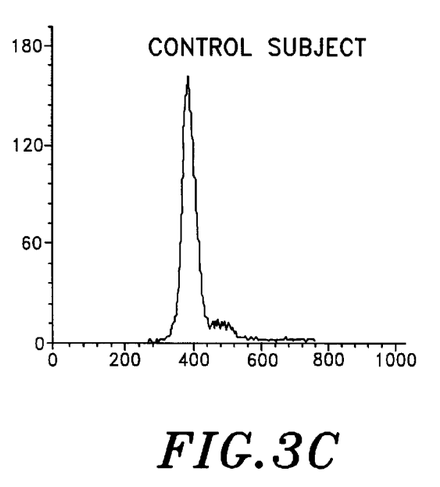
Figure 3D:
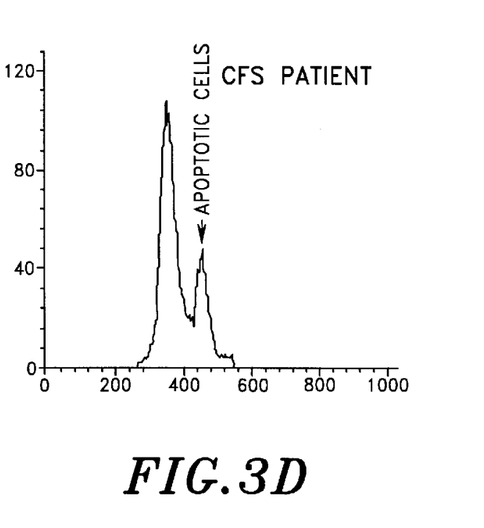

PKR protein levels were greatly increased in CFS individuals (n=30) as compared to healthy control individuals (2.7±0.26 and 0.89±0.18, respectively) (P<0.001, Mann-Whitney U-Test) (FIG. 2).

To determine whether PBMC isolated from CFS individuals contained elevated levels of apoptotic cells compared to healthy controls, PBMC were analyzed by flow cytometry as described below.

EXAMPLE 7

Detection of Apoptosis by Flow Cytometry

The rate of apoptosis was determined by flow cytometry using the Apo-direct™ kit (Phoenix Flow Systems, San Diego, Calif.) as described by the manufacturer. The procedure used is essentially as described by Gorczyca et al. (*Int. J. Oncol.*, 3: 627–634, 1993, incorporated by reference). Briefly, PBMC from CFS and control individuals (1–2×10$^6$ cells/culture) were cultured in RPMI-1640 supplemented with 10% fetal calf serum (FCS) and 2% penicillin-streptomycin. In certain experiments, the PKR inhibitor 2-AP was added to the cultures. Cells were incubated for 12 hours at 37° C. in a humidified 5% $CO_2$ incubator. The cells were harvested, centrifuged (10,000× g, 5 min., room temperature) and washed twice with PBS (5 ml per wash). Paraformaldehyde (1% w/v) was added to the cells, followed by a 15 minute incubation on ice. The cells were pelleted by centrifugation, washed twice with PBS (5 ml per wash) fixed with ice cold 70% ethanol and incubated at −20° C. overnight. Fixed cells, positive controls (HL-60 cells treated with camptotecin I, an inducer of apoptosis) and negative controls (untreated HL-60 cells) were labeled with fluorescent-tagged deoxyuridine triphosphate (F-dUTP) and stained with propidium iodide (PI). F-dUTP, in the presence of terminal deoxynucleotidyl transferase (TdT), labels the 3' hydroxy termini ends of DNA resulting from numerous strand breaks in apoptotic cells. PI stains cellular DNA. Cells were analyzed using a Becton-Dickinson FACScan flow cytometer for red (propidium iodide) and green (fluorescein) emissions. Unstained cells were gated from the analysis.

Figure 4:
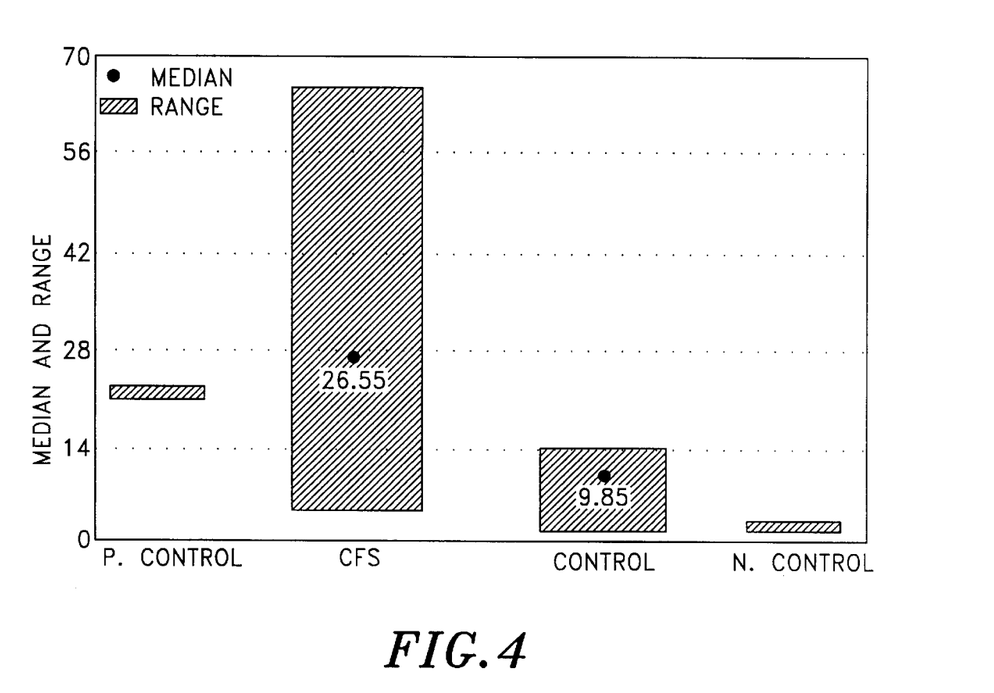
FIG. 4 shows a statistical analysis of the apoptotic cell population in CFS individuals compared to healthy control subjects.
Figure 5A:
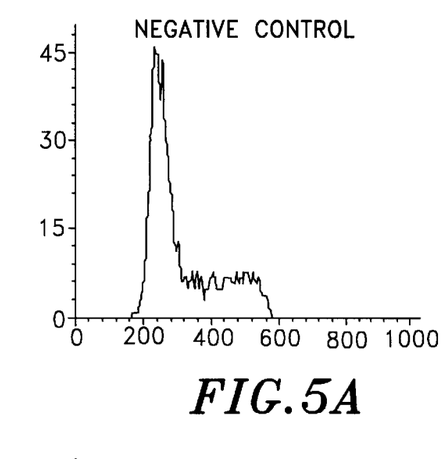
FIG. 5 shows the inhibition of apoptosis in CFS individuals by the PKR inhibitor 2-aminopurine (2-AP).
Figure 5B:
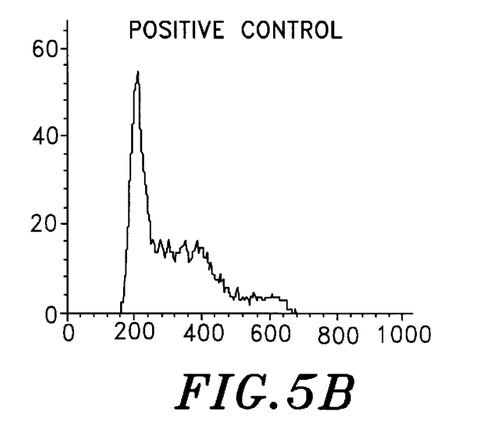
Figure 5C:
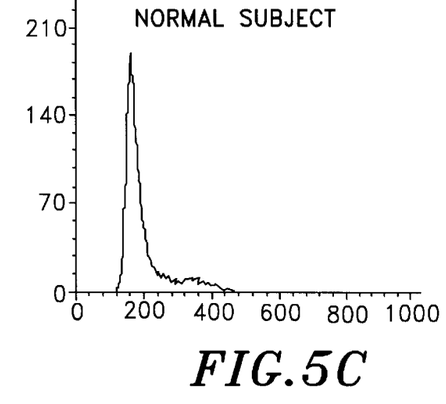
Figure 5D:
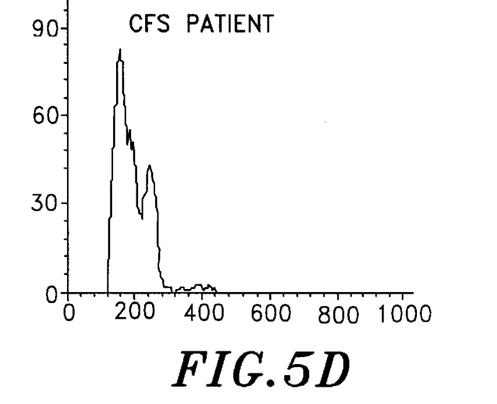
Figure 5E:
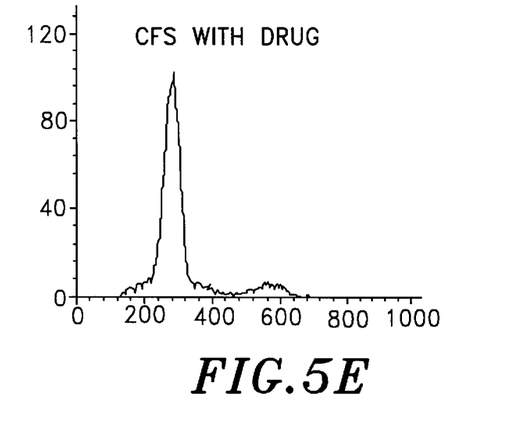

A subpopulation of apoptotic cells, characterized by fractional DNA content, was present on the DNA frequency histograms of the positive control and CFS patient (FIG. 3). In contrast, little or no apoptotic cells were detected in healthy control individuals. Quantitative analysis of apoptotic cell populations in CFS individuals (n=30) showed a statistically significant increase as compared to healthy control individuals (n=15) (26.6%±3.7% and 9.9%±4.2%, respectively) (FIG. 4). The population of apoptotic cells in 73% of CFS individuals (22/30) was well above the apoptotic cell population in the positive control cells. Approximately 3–5% of cells normally undergo spontaneous apoptosis in untreated cultures.

Figure 6:
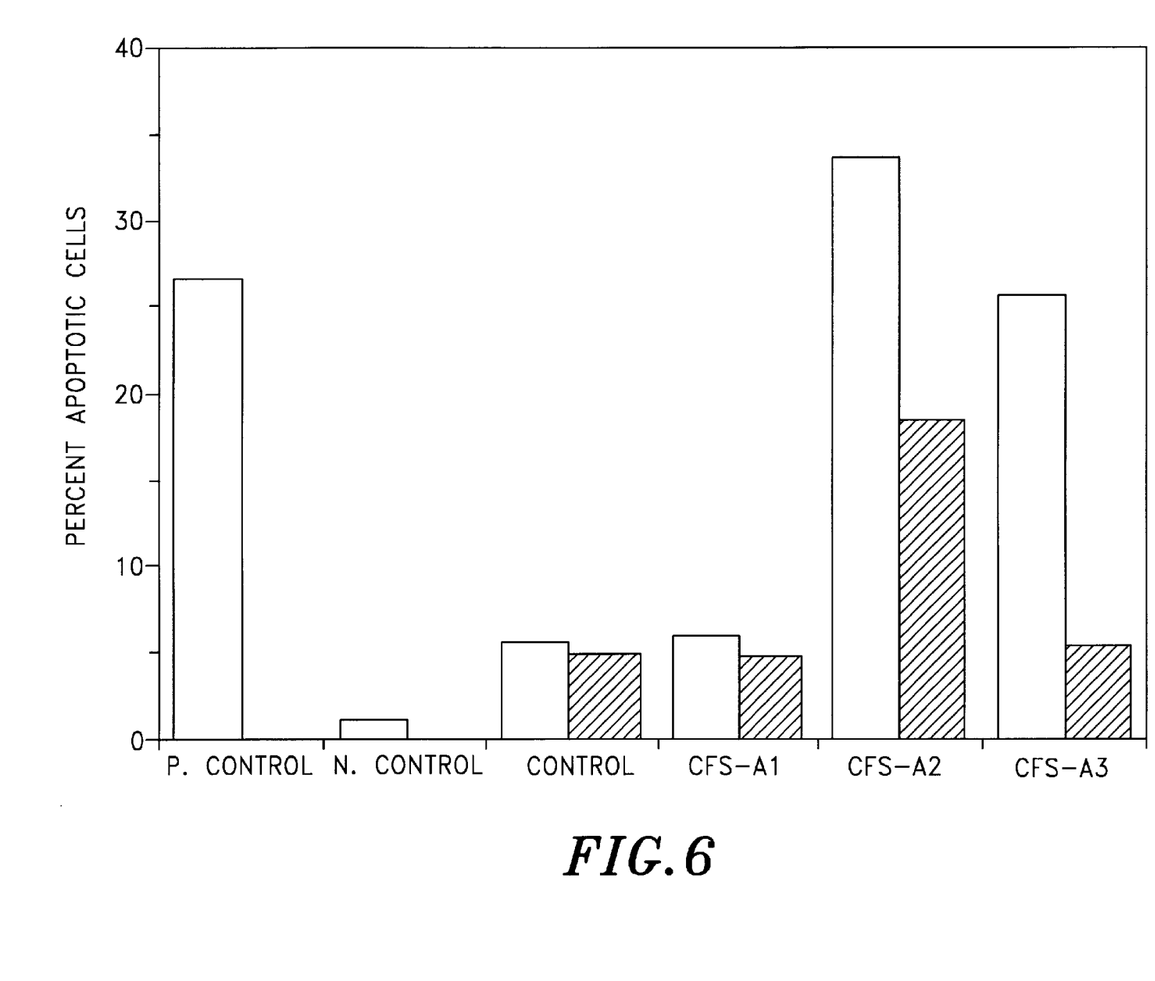
FIG. 6 shows the effect of 2-AP on the inhibition of apoptosis in CFS individuals compared to healthy control individuals. The hatched bars represent treatment with 2-AP.
Figure 7:
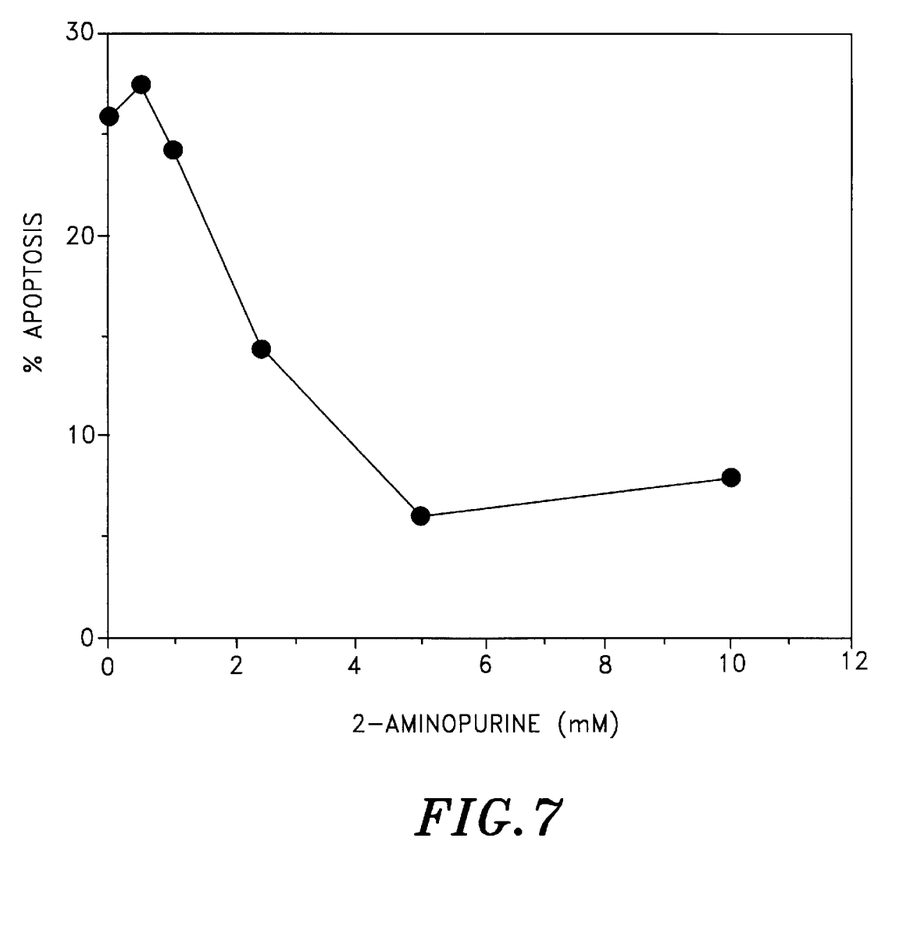
FIG. 7 shows the dose-dependent inhibition of apoptosis by 2-AP in CFS individuals.

2-AP (5 mM) decreased the apoptotic cell population in CFS individuals. In 50% of the apoptotic samples, 2-AP reduced the apoptotic population by more than 60% (FIG. 5). 2-AP is a potent inhibitor of PKR autophosphorylation. In CFS patients with high PKR levels (i.e. patients A2 and A3), 2-AP reduced the population of apoptotic cells (FIG. 6). In contrast, in patients with moderate or normal PKR levels (i.e. patient A1), 2-AP did not reduce their apoptotic cell population. 2-AP decreased the apoptotic cell population in CFS individuals in a dose dependent manner with an $ID_{50}$ of 2.5 mM (FIG. 7). The diluent used to prepare 2-AP stock solution had no effect on PKR autophosphorylation or the population of apoptotic cells, indicating that the inhibition was indeed caused by 2-AP.

To determine whether the induction of apoptosis in PBMC isolated from CFS individuals represents a discrete block in cell cycle progression, PBMC isolated from CFS and control individuals were analyzed as described below.

EXAMPLE 8

Cell Cycle Analysis

PBMC isolated from control and CFS individuals were processed and ethanol fixed as described in Example 7. The fixed cells were prepared for cell cycle analysis. Briefly, cells were resuspended in 100 µl RNase A (Sigma)—PBS solution containing 180 µg RNase A/ml and incubated at room temperature for 30 min. The RNase A solution was replaced with 1 ml PI solution (50 µg/ml in PBS with 0.1% Triton™ X-100). PI staining was preformed for 15 min at room temperature in the dark. Fluorescence measurements were performed using the 488 nm line on an argon laser operating at 500 mW. Data were collected into a two parameter histogram showing light scatter versus red fluorescence and gated to eliminate any particles that were not the correct size for intact cells.

The non-apoptotic cell population in PBMC isolated from CFS individuals consisted of cells arrested in the late S and G2/M boundaries as compared to healthy controls. The arrest was characterized by increased S (9 to 23%) and G2/M (4 to 24%) phases of the cell cycle (Table 1). Such an abnormality in cell cycle progression is an indication of abnormal mitotic cell division.

TABLE 1

| Phase | Control | CFS | CFS + 2-AP |
|---|---|---|---|
| $G_0/G_1$ | 88.6 ± 1.4 | 58.9 ± 2.4 | 87.4 ± 3.6 |
| S | 8.6 ± 1.2 | 22.8 ± 2.4 | 7.6 ± 3.1 |
| $G_2/M$ | 3.6 ± 0.82 | 24.3 ± 3.4 | 4.9 ± 2.9 |

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A method of detecting chronic fatigue syndrome (CFS) in an individual, comprising the steps of:
    isolating peripheral blood mononuclear cells (PBMCs) from said individual;
    determining the number of apoptotic PBMCs present in PBMCs from said individual by fluorescently or radioactively labeling DNA strand breaks in said PBMCs and detecting said labeled strand breaks by flow cytometry; and
    comparing said number of apoptotic PBMCs present in PBMCs from said individual to an expected amount of apoptotic PBMCs from a control individual known not to have CFS, wherein an increase in said number of apoptotic PBMCs in said individual compared to said amount of apoptotic PBMCs from said control individual indicates the presence of CFS.

2. A method of detecting chronic fatigue syndrome (CFS) in an individual, comprising the steps of:
    isolating peripheral blood mononuclear cells (PBMCs) from said individual;
    determining the number of PBMCs from said individual arrested in the late S and $G_2/M$ stages of the cell cycle; and
    comparing said number of arrested PBMCs from said individual to an expected number of arrested PBMCs from an individual known not to have CFS, wherein an increase in said number of arrested PBMCs in said individual compared to said number of arrested PBMCs from said control individual indicates the presence of CFS.

3. The method of claim 2, wherein said determining step comprises fluorescent labeling of said PBMCs and detection of said labeled PBMCs by flow cytometry.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 576 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:1:

```
GGATCCCCGC AAGTGAAATC TCCTCCGTCT TGGAGAAGGG AGAGCGTTTG CCCCAGCCAC      60
CCATTTGTAC CATTGATGTG TACATGATCA TGGTCAAATG CTGGATGATT GATGCAGACA     120
GCCGTCCCAA GTTTCGTGAG CTGATTGCAG AGTTCTCCAA AATGGCTCGT GACCCTCCCC     180
GCTATCTTGT TATACAGGGA GATGAAAGGA TGCACTTGCC TAGCCCTACA GATTCCAAGT     240
TTTATCGCAC CCTGATGGAG GAGGAGGACA TGGAAGACAT TGTGGATGCA GATGAGTATC     300
TTGTCCCACA CCAGGGCTTT TTCAACATGC CTCTACATC  TCGGACTCCT CTTCTGAGTT     360
CATTGAGCGC TACTAGCAAC AATTCTGCTA CAAACTGCAT TGACAGAAAT GGGCAGGGGC     420
ACCCTGTGAG GGAAGAGGCT TCCTGCCTGC TCCAGAGTAT GTAAACCAGC TGATGCCCAA     480
GAAACCATCT ACTGCCATGG TCCAGAATCA AATCTACAAC TTCATCTCTC TCACAGCAAT     540
CTCAAAGCTC CCCATGGACT CAAGATACCA GAATTC                              576
```

( 2 ) INFORMATION FOR SEQ ID NO:2:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:2:

```
GGTCAAAGAC TAAGTGCCCG CAAGTGAAAT CCTCCTCCG       39
```

( 2 ) INFORMATION FOR SEQ ID NO:3:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:3:

```
CCTTTCTGTT TCTGCAGCTG GTATCTTGAG TCCATGGG       38
```

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: cDNA (x i) SEQUENCE DESCRIPTION: SEQ ID NO:4:

GGTCAAAGAC TAAGTGCC                                                                 18

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear     (i i) MOLECULE TYPE: cDNA     (x i) SEQUENCE DESCRIPTION: SEQ ID NO:5:

CCTTTCTGTT TCTGCAG                                                                  17

(2) INFORMATION FOR SEQ ID NO:6:

(i) SEQUENCE CHARACTERISTICS:
        (A) LENGTH: 19 amino acids
        (B) TYPE: amino acid
        (C) STRANDEDNESS: single
        (D) TOPOLOGY: linear     (i i) MOLECULE TYPE: peptide     (x i) SEQUENCE DESCRIPTION: SEQ ID NO:6:

His Val Lys Ala Leu Ala Lys Leu Asp His Val Asn Ile Val His Tyr
1               5                   10                  15

Asn Gly Cys (2) INFORMATION FOR SEQ ID NO:7:

(i) SEQUENCE CHARACTERISTICS:
        (A) LENGTH: 19 amino acids
        (B) TYPE: amino acid
        (C) STRANDEDNESS: single
        (D) TOPOLOGY: linear     (i i) MOLECULE TYPE: peptide     (x i) SEQUENCE DESCRIPTION: SEQ ID NO:7:

Cys Tyr Ile Gly Leu Ile Asn Arg Ile Ala Gln Lys Lys Arg Leu Thr
1               5                   10                  15

Val Asn Tyr